(12) United States Patent
Hommann et al.

(10) Patent No.: US 7,806,866 B2
(45) Date of Patent: Oct. 5, 2010

(54) DEVICE FOR AUTOMATICALLY INJECTING AN ACTIVE AGENT

(75) Inventors: Edgar Hommann, Grossaffoltern (CH); Benjamin Scherer, Uster (CH); Lorenz Broennimann, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 11/134,044

(22) Filed: May 20, 2005

(65) Prior Publication Data

US 2005/0277886 A1    Dec. 15, 2005

Related U.S. Application Data

(63) Continuation of application No. PCT/CH03/00755, filed on Nov. 17, 2003.

(30) Foreign Application Priority Data

Nov. 25, 2002  (CH) ...................... 1984/02
May 13, 2003   (CH) ...................... 0837/03

(51) Int. Cl.
  *A61M 5/20* (2006.01)
  *A61M 5/00* (2006.01)
(52) U.S. Cl. ...................... 604/136; 604/187
(58) Field of Classification Search ............ 604/218, 604/295, 500, 512, 181, 110, 134–137, 156–157, 604/187, 194, 196, 171, 192, 197, 198, 228, 604/232, 235, 207
See application file for complete search history.

(56) References Cited

U.S. PATENT DOCUMENTS

| 5,320,609 | A | * | 6/1994 | Haber et al. ............... 604/135 |
| 5,378,233 | A |   | 1/1995 | Haber et al. |
| 5,478,316 | A | * | 12/1995 | Bitdinger et al. ........... 604/135 |
| 5,593,390 | A | * | 1/1997 | Castellano et al. ......... 604/187 |
| 6,099,503 | A | * | 8/2000 | Stradella .................... 604/135 |
| 6,203,530 | B1 | * | 3/2001 | Stewart, Sr. ................. 604/207 |
| 6,936,032 | B1 | * | 8/2005 | Bush et al. .................. 604/187 |
| 2002/0095120 | A1 | * | 7/2002 | Larsen et al. ............... 604/187 |
| 2004/0210199 | A1 | * | 10/2004 | Atterbury et al. ........... 604/224 |

FOREIGN PATENT DOCUMENTS

WO    WO 02/083218 A1    10/2002

* cited by examiner

*Primary Examiner*—Kevin C Sirmons
*Assistant Examiner*—Catherine N Witczak
(74) *Attorney, Agent, or Firm*—Dorsey & Whitney LLP; David E. Bruhn, Esq.

(57) ABSTRACT

A device for automatically injecting an active agent, the device involving a syringe filled with an active agent and carrying an injection needle, the syringe displaceable in a receiver by the tension of a spring. A transmission displaceable by at least one spring traverses a first partial path for sticking the injection needle and a second partial path for emptying the active agent from the syringe. The at least one spring acts between the transmission and an intermediate part, and another spring acts between the intermediate part and a support fixedly connected to the receiver. An indicator visible from the outside is connected to the intermediate part, moves only during the second partial path, and traverses a path length that is substantially smaller that the sum of both partial paths.

11 Claims, 8 Drawing Sheets

FIG. 6
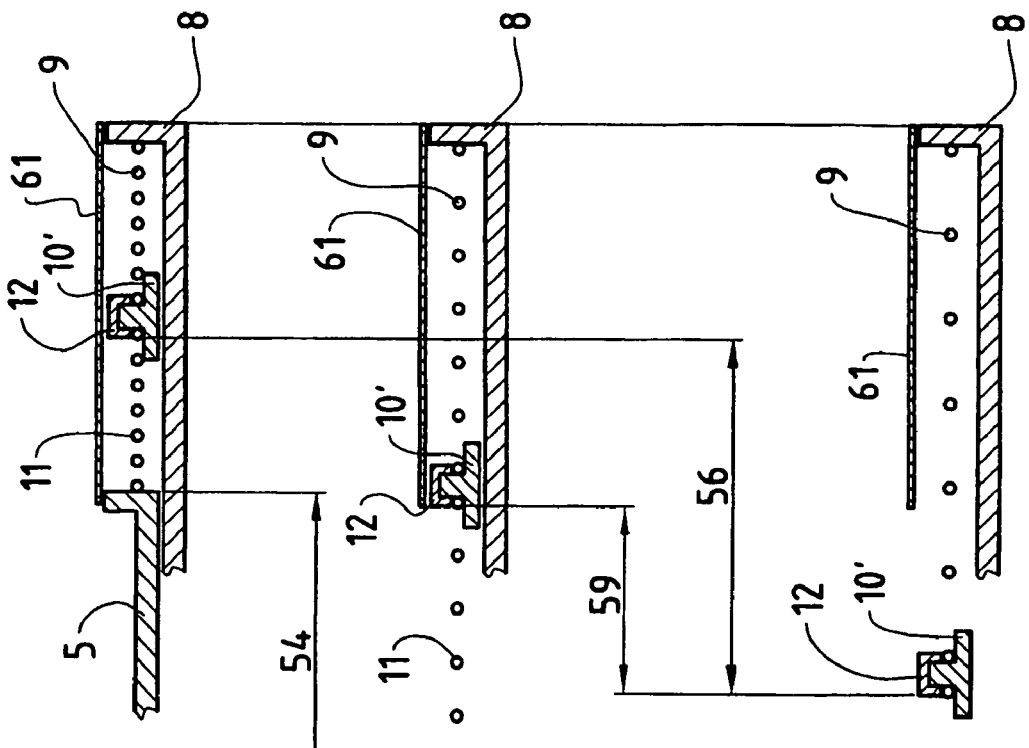
FIG. 6A
FIG. 6B
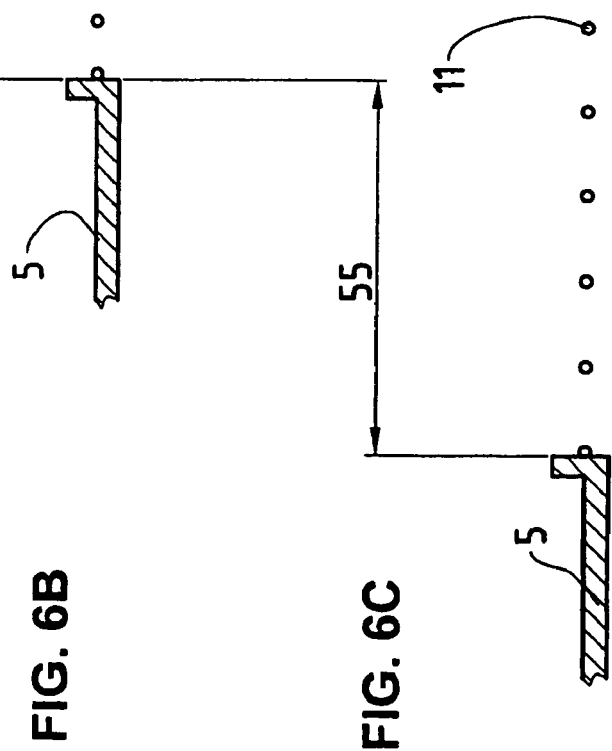
FIG. 6C

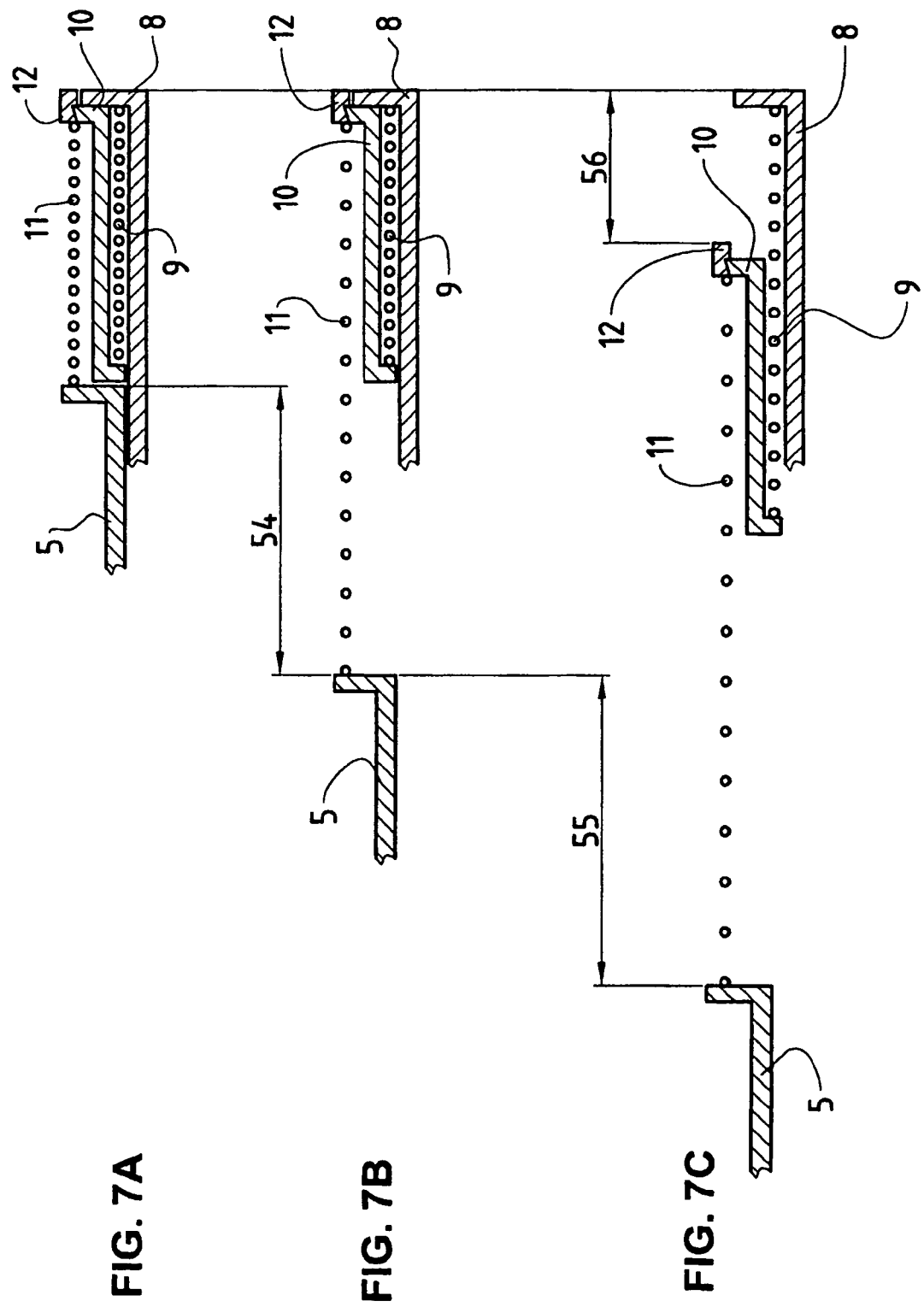

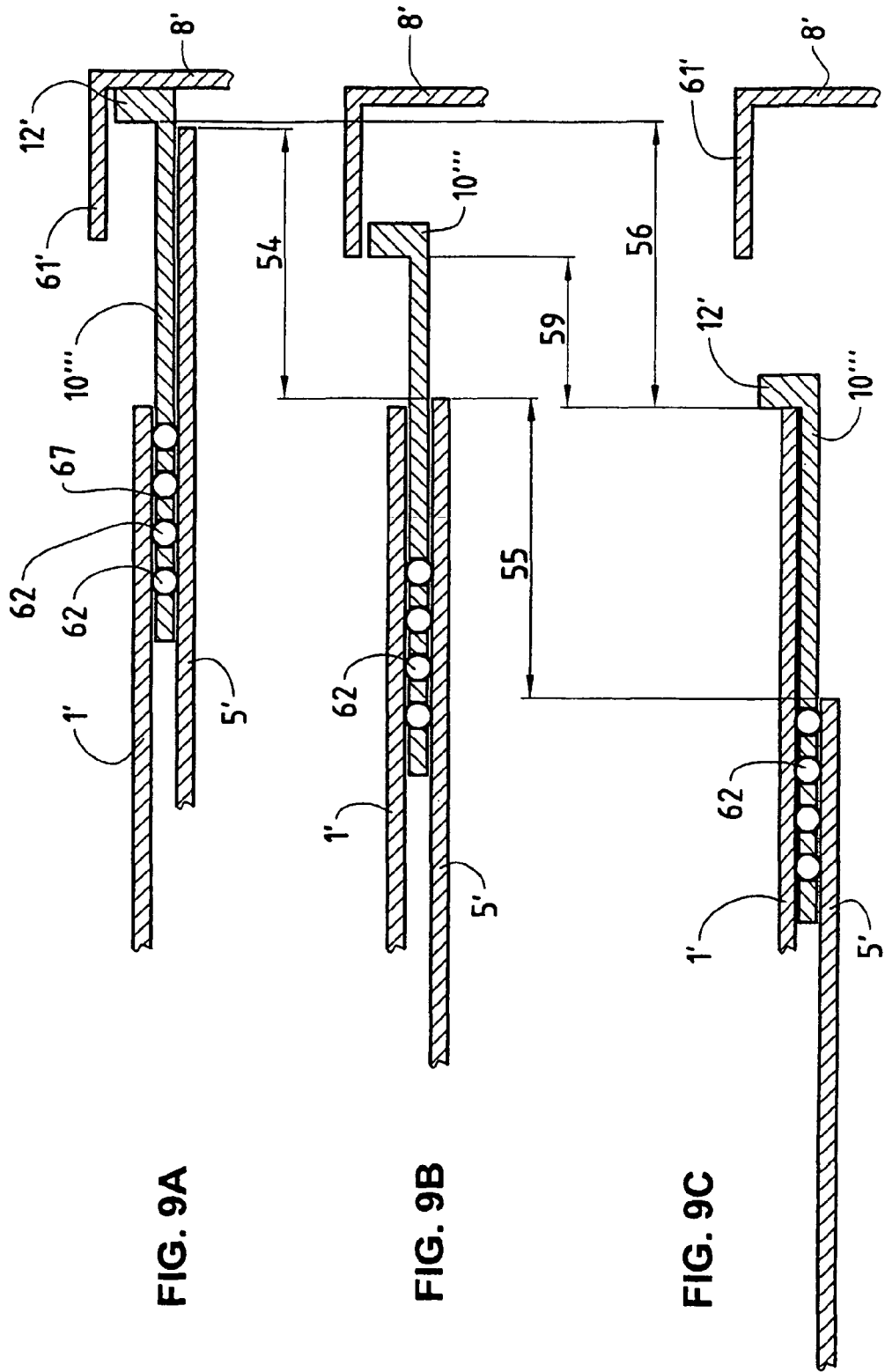

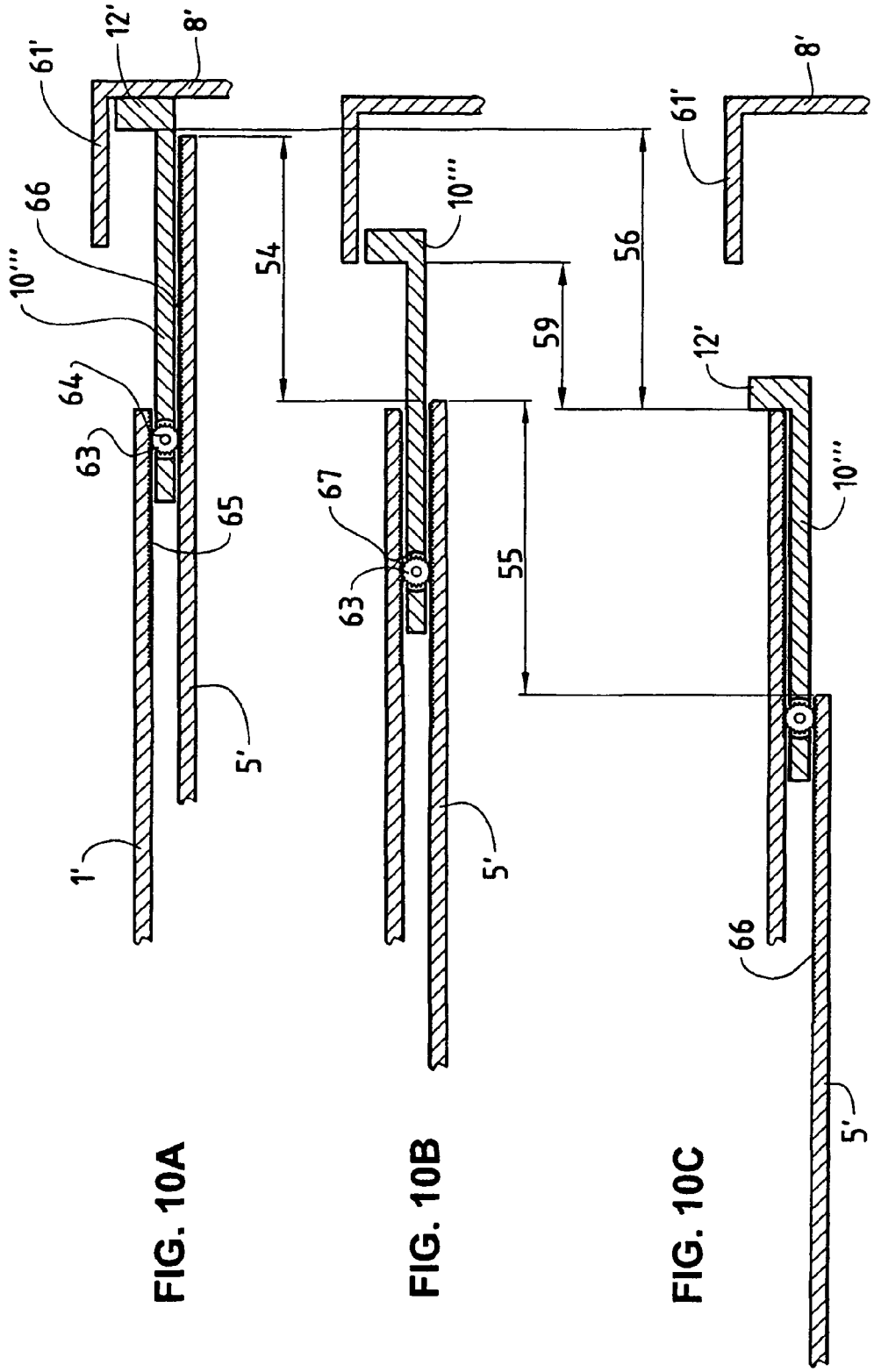

DEVICE FOR AUTOMATICALLY INJECTING AN ACTIVE AGENT

CROSS-REFERENCE TO RELATED APPLICATION(S)

This application is a continuation of International Application No. PCT/CH2003/000755, filed on Nov. 17, 2003, which claims priority to Swiss Patent Application No. 1984/02, filed on Nov. 25, 2002 and Swiss Patent Application No. 837/03, filed on May 13, 2003, the contents of which are incorporated herein by reference in their entirety.

BACKGROUND

The application relates to a device for automatically injecting an agent, having a receptacle for the agent, which receptacle, along with an injection needle connected to the latter, is displaceable in a housing for the purpose of inserting the injection needle, and having a syringe piston that is displaceable in the receptacle for the purpose of expelling the agent.

Devices of the type mentioned above, so-called autoinjectors, are known in many kinds of embodiments. In particular, they serve to administer medication that the patient in question himself injects. A problem of such autoinjectors that has until now been solved only unsatisfactorily consists in the fact that the patient, after the insertion of the injection needle initiated by himself, does not know how long the expelling of the medication lasts and when he can pull the injection needle out again. A possible solution to this problem consists in connecting to the syringe piston an indicator element visible from the outside. Since, however, the syringe piston already, before the expelling of the medication, covers the distance required for the insertion of the injection needle, an indicator element connected directly to the syringe piston could easily give rise to misinterpretations and/or could increase the structural length of the autoinjector in an undesirable manner.

It is therefore a task of the present invention to provide a device of the type mentioned above, in which device it can be unambiguously determined from the outside when the injection process has ended, and which has no significant effect on the structural length of the autoinjector.

SUMMARY

In one embodiment, the present invention addresses the above task by providing a device for automatically injecting an active agent, the device involving a syringe filled with an active agent and carrying an injection needle, the syringe displaceable in a receiver by the tension of a spring. A transmission displaceable by at least one spring traverses a first partial path for sticking the injection needle and a second partial path for emptying the active agent from the syringe. The at least one spring acts between the transmission and an intermediate part, and another spring acts between the intermediate part and a support fixedly connected to the receiver. An indicator visible from the outside is connected to the intermediate part, moves only during the second partial path, and traverses a path length that is substantially smaller that the sum of both partial paths.

In one embodiment, a displacement path of the indicator visible from the outside is shorter than the total displacement distance of a syringe piston in relation to the housing. This reduction in the travel of the path of the syringe piston to the indicator increases the freedom of design in the structuring of the indicator, because the indicator traverses or travels a path that is not directly dependent on the path of the syringe piston.

According to an embodiment of the present invention, a transmission part displaceable through at least one spring element is present, which transmission part is capable of carrying out a first partial path for inserting the injection needle and a second partial path for expelling the agent such that the at least one spring element is effective between the transmission part and a support part immovably connected to the housing, and such that the indicator is connected to the spring element at a location between the two ends of the spring element. This embodiment allows the device of the present invention to be achieved in a structurally especially simple and cost-effective manner.

According to a further embodiment of the invention, a transmission part displaceable through at least one spring element is present, which transmission part is capable of carrying out a first partial path for inserting the injection needle and a second partial path for expelling the agent, the at least one spring element is effective between the transmission part and an intermediate part, at least one additional spring element is effective between the intermediate part and a support part immovably connected to the housing, and the indicator is connected to the intermediate part. Through this serial connection of at least two spring elements with the interposition of an intermediate part, it is possible to design the path of the indicator in a practically free manner, so that, for example, autoinjectors can be constructed in which different syringes, especially syringes having different content amounts, can be used, and in which autoinjectors consequently the path of the syringe piston required for expelling the amount of medication present in the syringe can also be changed.

Provided according to a further embodiment of the present invention is a cover that covers the indicator when the transmission part carries out the first partial path. Through this means, the indicator is visible only after the beginning of the expelling and the user can observe the expelling course without being distracted by the movement of the indicator during the insertion of the injection needle.

According to a further embodiment of the invention, a stop limits the stressing of the additional spring to a maximum spring force, and the springs are dimensioned such that the maximum spring force of the stressed additional spring corresponds to the instantaneous spring force of the at least one spring after the insertion of the injection needle and before the expelling of the agent. In consequence of this, the intermediate part moves only during the second partial path, i.e., only during the expelling of the agent. The stop can also be realized in that the additional spring is a compression spring that is compressed to its block length.

Provided according to another embodiment of the invention is an additional stop that also limits the relaxing of the additional spring, so that the path covered by the indicator is fixed. The indicator thereby moves in a defined range independent of the length of the second partial path. This makes possible the use of receptacles having different volumes of contents.

According to another advantageous embodiment of the invention, the indicator is formed in the shape of a ring. The indicator is thereby visible around the device from any direction, so that the user need not pay attention to the rotational position of the device before he places it into position for making an injection.

According to a further embodiment of the invention, the at least one spring and the additional spring are arranged coaxially and, at least in the stressed state, are situated at least partially telescopically one in another. This makes possible a space-saving design for the device, and ensures that the device does not become unmanageably long due to the springs that work in conjunction with the indicator.

In another embodiment of the invention, a transmission part displaceable through at least one spring element is present, which transmission part is capable of carrying out a first partial path for inserting the injection needle and a second partial path for expelling the agent such that the indicator is connected to an intermediate part that, in turn, is connected to at least one rolling element, which during the movement of the transmission part shifts between the transmission part and a region that is immovably connected to the housing. The rolling element or elements traverse(s) half of the path that the transmission part traverses. In order to avoid an undesired sliding of the at least one rolling element, it, according to a further embodiment of the invention, displays on its periphery teeth or other suitable surface characteristic that meshes with teeth arranged on the transmission part and on the region immovably connected to the housing.

In another embodiment of the invention, the indicator is located in the rear end region of the device, i.e., the end opposite to that of the injection needle. This arrangement offers a good visibility of the indicator with comfortable handling of the device, which is usually held onto by the user with one hand during operation. In this case, the rear end with the indicator protrudes beyond the hand of the user.

When, according to a further embodiment of the invention, the indicator is visible from the outside through a transparent or translucent part, a closed design of the device becomes possible, in particular a design having no slits or the like, so that the high hygienic requirements typical of this field can be met.

BRIEF DESCRIPTION OF THE DRAWINGS

FIG. 6, including FIGS. 6A-6C, depicts one embodiment of an indicator;

FIG. 7, including FIGS. 7A-7C, depicts a second embodiment of an indicator, as incorporated into the type of autoinjector illustrated in FIGS. 1 to 5;

FIG. 9, including FIGS. 9A-9C, depicts another embodiment of an indicator; and

FIG. 10, including FIGS. 10A-10C, depicts another embodiment of an indicator.

DETAILED DESCRIPTION

Figure 1:
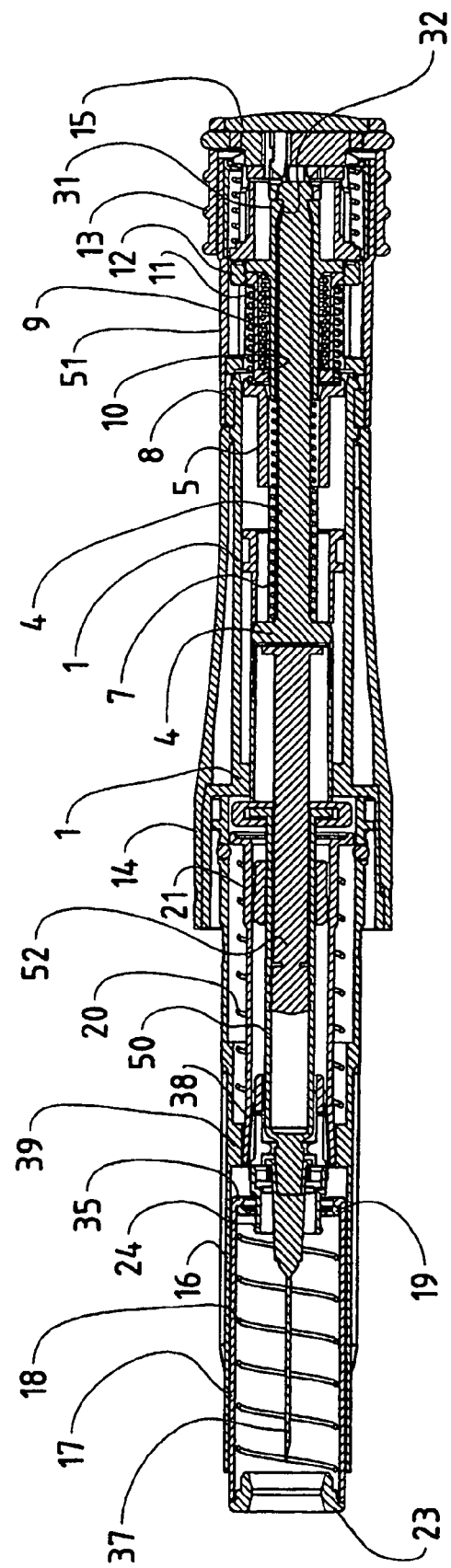
FIG. 1 is a longitudinal section through an exemplary embodiment of an autoinjector according to the present invention in the loaded state.

The autoinjector consists of two main components, namely the reservoir part, shown on the left in the drawings, that accommodates a filled syringe, and the power pack, shown on the right in the drawings, in which the parts serving the automatic insertion and emptying of the syringe are installed or located. The two main components are detachably connected to each other via a bayonet-type connection between a receiving sleeve 16 and a power sleeve 1. In the following description, the side or end of the autoinjector at which the injection needle is located is referred to as the front.

With the aid of FIG. 1, which shows an embodiment of an operationally-ready autoinjector, the power pack is now described first. The parts for the driving of the autoinjector are accommodated in the grip sleeve 14, to the rear end of which an indicator window 51 is attached. The indicator window 51 is produced of transparent or translucent material or has openings, for example in the form of slits, that allow the indicator 12 displaceably accommodated in the indicator window 51 to be observed from the outside. The indicator 12 has a ring-shaped design and is thus visible from any direction around the autoinjector. Arranged at the rear end of the autoinjector is the actuation head 13, which is provided at its rear face side with a cover disc 15. Accommodated inside the grip sleeve 14 is the power sleeve 1. At its rear end, the power sleeve 1 is connected to a catch sleeve 8 by means of a snap connection. The catch sleeve 8, for its part, displaceably accommodates in its interior a spring sleeve 10. The spring sleeve 10 is coupled at the rear to the indicator 12 through a snap connection. At the front side of the spring sleeve 10, a transmission part 5 is displaceably supported in the power sleeve 1. The transmission part 5 has the task of actuating the piston rod 52 of the syringe 50 in order to expel the contents of the syringe, as will be described more precisely later. Accommodated inside the spring sleeve 10 is a spring 9 in the stressed state, which spring rests on the spring sleeve 10 at the front and presses against the catch sleeve 8 at the rear. A second spring 11, likewise in the stressed state, is located on the outside of the spring sleeve 10, and rests on the transmission part 5 at the front and presses against the spring sleeve 10 at the rear.

A piston guide 4 is situated with its front, sleeve-shaped end against the collar of the syringe and extends through the transmission part 5, the spring sleeve 10, and the catch sleeve 8 into the region of the actuation head 13. The piston guide 4 is prestressed towards the front through a spring 7, which at the rear rests against the catch sleeve 8. At its rear end, the piston guide 4 is held in the position shown in FIG. 1 by two catch lobes 31 formed on the catch sleeve 8, which lobes engage a groove 32 formed on the rear end of the piston guide 4. Catch elements, for example balls 6, that are accommodated in radial openings 33 of the piston guide 4 and engage recesses 34 in the transmission part 5, ensure in this operating position that the transmission part 5 and the piston guide 4 can move only in common. It should be understood that instead of balls 6, other catch elements, for example pins, could also be used.

The description of reservoir part now follows. The parts for the accommodation syringe 50 are, as mentioned, installed in the receiving sleeve 16, which is connectable to the power sleeve 1, as described. A sliding sleeve 21 receives into itself the syringe with the interposition of a needle holder 22. The needle holder 22 ensures, in the case of Luerslip couplings, that the injection needle 37 cannot be removed from the syringe so long as the latter is situated in the autoinjector. At the front, the needle holder 22 rests against a support ring 24 connected to the sliding sleeve 21. In the case of syringes and needles having Luer-lock couplings, in which therefore the injection needle is connected to the syringe by means of a thread, no needle holder 22 is present. The sliding sleeve 21 is displaceable within the receiving sleeve 16 and is pressed into the operating position shown in FIG. 1 by a spring 20. A sleeve-shaped needle protector 17 is displaceable within the receiving sleeve 16. The needle protector 17 is closed at the front by a snap cover 23, which leaves open a passage for the injection needle, and at its rear end has an inward-pointing flange 35. A spring 18 rests against the snap cover 23 at the front and at the rear against a carrier ring 19, which in turn is held on the support ring 24. In this drawing, the spring 18 is in its relaxed state.

Figure 2:
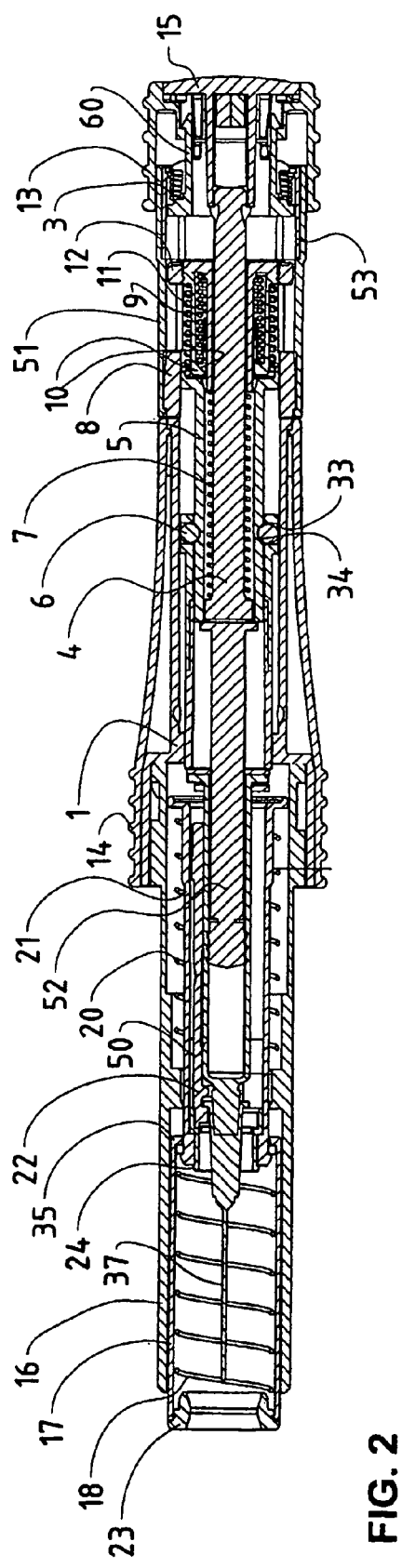
FIG. 2 is a longitudinal section through the autoinjector in the unlocked state, the sectional plane being rotated by 90° with respect to FIG. 1.

For the preparation for the injection, the autoinjector must be brought from the secured state shown in FIG. 1 into the unlocked state, which is shown in FIG. 2. For this purpose, the actuation head 13 is moved toward the rear. This can take place in that the device is grasped with one hand on the receiving sleeve 16 and the other hand on the actuation head 13, and the two parts are pulled away from each other. Through the design and arrangement of the actuation head 13, it is also possible to hold onto the autoinjector at the grip sleeve 14 and push the actuation head 13 toward the rear with the thumb of the same hand. Circumferential ribs provided on the actuation head 13 prevent a slipping off of the thumb in this case. This rearward pushing of the actuation head 13 may be referred to as the unlocking movement. In this process, at the front edge of the actuation head 13 a region of the indicator window 41 becomes uncovered, on the inside of which region a conspicuously-colored warning sleeve 53 becomes visible, which warning sleeve clearly indicates that the autoinjector is now unlocked and is ready for the injection. In the unlocking movement, tongues 36, formed inwardly on the cover disc 15 of the actuation head 13, slide over the catch lobes 31 formed on the catch sleeve. The tongues and the catch lobes are formed such that during the unlocking movement the tongues 36 give way elastically in a radial direction while sliding over the ends of the catch lobes 31, which hold the piston guide 4 in place by engaging the above-mentioned groove 32. After the unlocking, the tongues 36 formed on the cover disc 15 are situated in the manner of wedges between the catch lobes 31. With the unlocking movement, a spring 3, acting between hooks formed on the catch sleeve 8 and a retaining part 60 fastened in the actuation head by means of a snap connection, becomes stressed and thus presses the actuation head into its initial position according to FIG. 1, thereby ensuring that the tongues 36 rest against the catch lobes 31 with a light prestress. The autoinjector is now ready for the injection and is placed onto the skin of the patient with the snap cover 23 at the desired location. The patient holds onto the autoinjector at the grip sleeve 14. The triggering of the injection now merely requires the actuation head 13 to be shifted forward, i.e., in the direction of the body of the patient.

Figure 3:
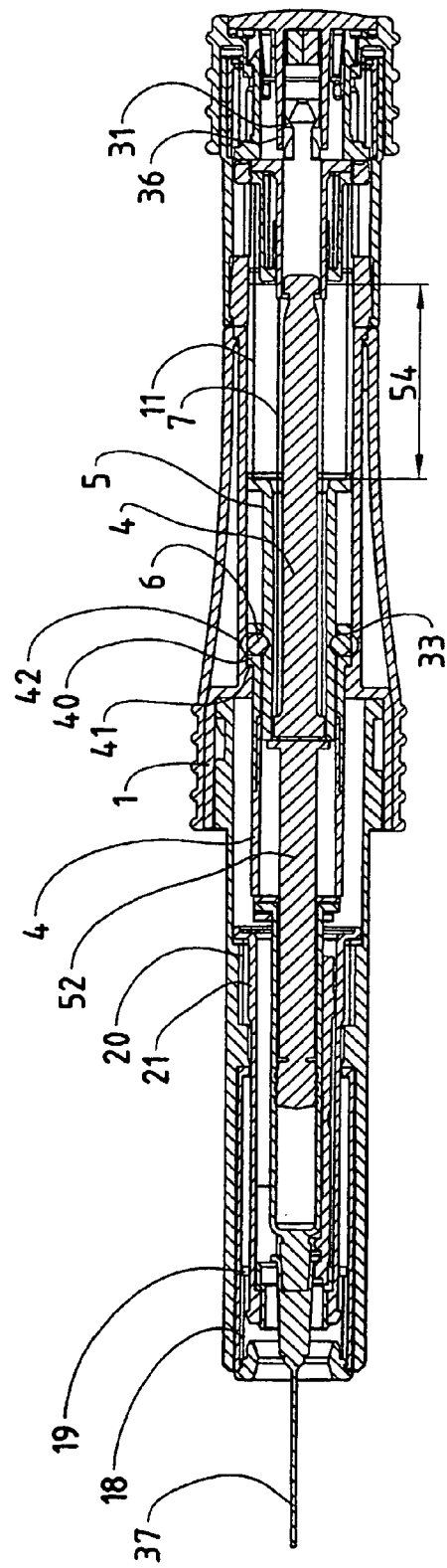
FIG. 3 is a longitudinal section through the autoinjector after the insertion of the injection needle, the section being made through the same plane as in FIG. 2.

In this triggering movement, the tongues 36 press between the catch lobes 31 and spread these radially apart, whereby the piston guide 4 is released and, through the force of the spring 7, thrust forward. The insertion movement is also aided by the force of the spring 11, which acts on the transmission part 5. Since the transmission part 5 is connected to the piston guide 4 via the balls 6, the relatively high initial force of spring 11 is thus added to that of spring 7 and reliably advance the needle to the full penetration depth. The force of the springs is also transferred via the sleeve-shaped front end of the piston guide 4 onto the collar of the syringe 50 and pushes the latter forward, together with the sliding sleeve 21 in which the syringe is accommodated, so that the injection needle 37 is advanced and penetrates the skin of the patient. In this movement, the sliding sleeve 21 compresses both the spring 20 and—via the carrier ring 19—the spring 18. The inserting path is limited by the resting of the shoulder 40 of the piston guide 4 against an inner shelf 41 of the power sleeve 1. In this end position, the openings 33 in the piston guide 4, which accept the balls 6, are aligned with the recesses 42 that are provided in the power sleeve 1, the balls 6 can give way to the outside, and the coupling between the piston guide 4 and the transmission part 5 is cancelled. Simultaneously, the piston guide 4 is now locked against the power sleeve 1, so that the force of the spring 20 is received by the power sleeve and thus does not counteract the force of the spring 7, which spring effects the expelling of the medication. Consequently, the injection can now automatically begin, the piston rod 52 of the syringe being further thrust forward by the transmission part 5 under the force of the springs 11 and 9. The spring 11 is designed to be so much stronger than the spring 9 that, up to the moment of the beginning of the injection, the spring sleeve 10 and the indicator 12 connected to the latter remain in the position shown in FIG. 3, in which position a stop is formed between an outwardly-projecting flange of the catch sleeve 8 and the spring sleeve 10. At this moment, the transmission part 5 has traversed the path indicated by 54 in FIG. 3. Simultaneously with the inserting movement, the spring 18 becomes stressed by the carrier ring 19 that has been moved towards the left in the drawings by the sliding sleeve 21.

Figure 4:
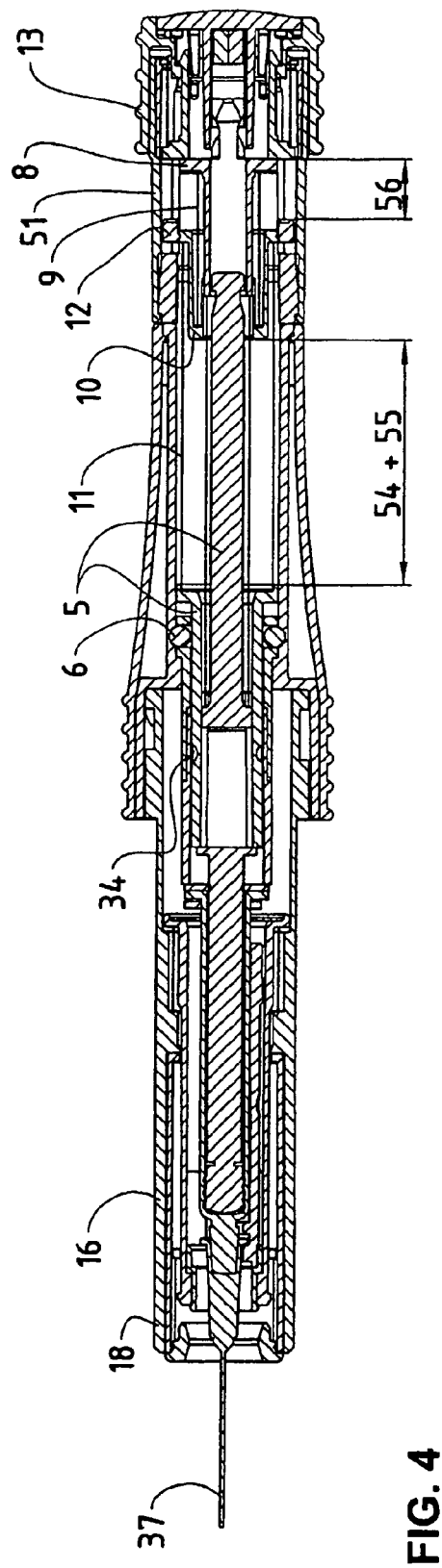
FIG. 4 is a longitudinal section through the autoinjector after the expelling of the medication, the section being made through the same plane as in FIGS. 2 and 3.

Upon the insertion of the injection needle 37, with the increasing path of the transmission part 5 the force of the spring declines to such an extent that the spring 9 can move the spring sleeve 10 off its stop against the catch sleeve 8 precisely at the moment when the piston guide 4 has reached its end position and the injection needle 37 has been fully inserted. The balls 6 now release the transmission part 5 such that the latter slips into the piston guide 4 and in the process can actuate the piston rod 52 of the syringe. The spring 9 now begins to expand. The spring 9 pushes the spring sleeve 10 forward, and with it the indicator 12, so that the indicator 12, after traversing the path 56, reaches its end position visible in FIG. 4 precisely at the moment when the piston rod 52 is also completely forward in the syringe 50 and consequently all of the fluid present in the syringe has been expelled. As a result, the user is able to follow the course of the injection process and sees, with the aid of the indicator 12 in the position shown in FIG. 4, that the entire content of the syringe has been expelled. In this, the path 56 of the indicator 12 is independent of the path of the piston rod 52 of the syringe 50 and can be substantially shorter than the path 54+55 of the transmission part 5. Through these means, an unnecessary length of the autoinjector is avoided, and syringes having different displacements can be used with the autoinjector. This design has the additional advantage that the relatively high initial force of the spring 11 is used for the inserting process, which process therefore takes place in a relatively slow manner, as is desired.

Figure 5:
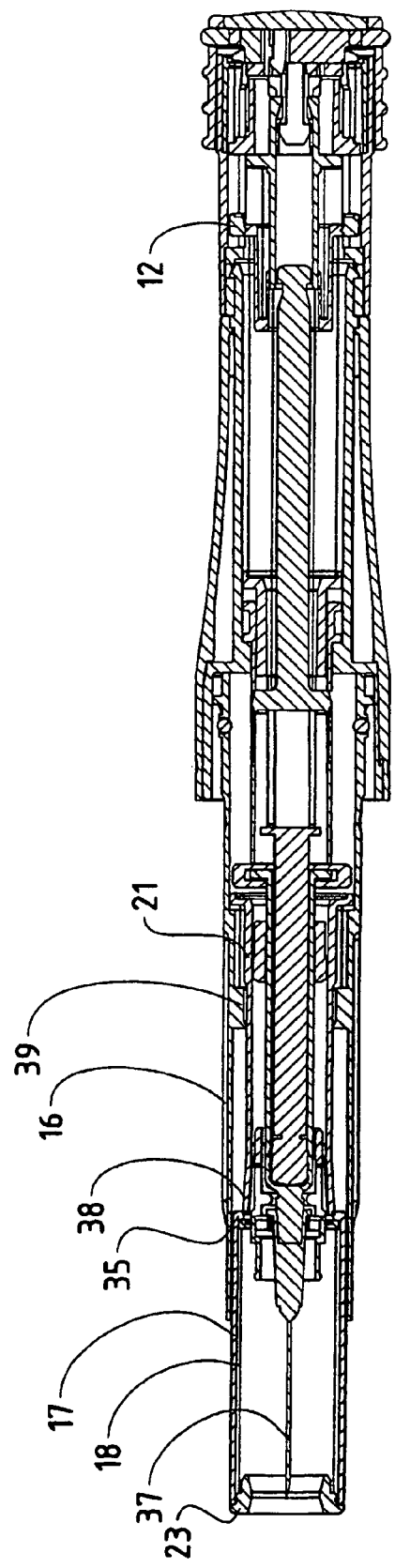
FIG. 5 is a longitudinal section through the autoinjector after the withdrawal of the injection needle, the section being made through the same plane as in FIG. 1.

Flexible tongues 38 provided in the sliding sleeve 21 are prevented, at the beginning of the inserting movement, from protruding outward by an inward-projecting, circular step 39 of the receiving sleeve 16. At the conclusion of the inserting movement, the flexible tongues project beyond the jacket surface of the sliding sleeve 21, as one can see in FIG. 5. After the indicator 12 has indicated the complete expelling of the medication, the user can withdraw the autoinjector. The spring 18, which had been prestressed during the inserting process, ensures that the needle protector 17 remains in contact with the skin of the patient during the withdrawing of the autoinjector. Thus, the needle protector 17 moves forward in relation to the receiving sleeve 16 until it completely covers the injection needle 37. The flexible tongues 38 snap out behind the flange 35 of the needle protector 17 and ensure that the latter cannot be pushed back into the receiving sleeve 16. Through these means, any danger of injury by the injection needle is eliminated.

Illustrated in FIGS. 6A-6C is an embodiment of an indicator. Although this embodiment form does not correspond exactly to that incorporated into the above-described exemplary embodiment of the autoinjector, component parts having the same function have the same reference numerals. The only exception is that the intermediate part, which in the embodiment according to FIGS. 1-5 is formed as the spring sleeve 10, has in FIGS. 6A-6C the reference numeral 10'. FIG. 6A shows the parts in the mutual, relative position that they assume in the stressed autoinjector that is ready for the injection. Starting from this position, the transmission part 5 moves to the left, as already described in reference to FIGS. 1 to 5. The catch sleeve 8, which as further described above is immovably connected to the grip sleeve 14, maintains its position in FIGS. 6A to 6C. Both of the represented springs, namely that spring acting between the catch sleeve 8 and the intermediate part 10' and the spring 11 acting between the intermediate part 10' and the transmission part 5, are stressed in the position shown in FIG. 6A. FIG. 6B shows the position of the parts with the injection needle 37 inserted. The transmission part 5 has displaced the sliding sleeve 21 along with the syringe 50 and in the process has moved forward by the path 54. Simultaneously, the intermediate part 10', along with the indicator 12, has moved proportionally by a magnitude that is substantially smaller than that of the path 54, as one can readily perceive in FIG. 6B. During the expelling of the medication, wherein the transmission part 5 moves further leftward by the path 55 until it reaches the end position according to FIG. 6C, the spring sleeve 10, and with it the indicator 12, likewise moves further in proportion to the transmission part 5, by the path 59. This path 59 of the indicator 12, which path thus shows the progress of the expelling of the medication, is of particular significance for the user. If the patient waits to withdraw the autoinjector until the indicator has reached its end position according to FIG. 6C, then a loss of part of the medication is reliably prevented. If one wishes to prevent the visibility from the outside of the path traversed by the indicator during the inserting, one can provide a cover 61, which opens a view onto the indicator 12 only after the expelling process begins.

FIGS. 7A-7C show a second embodiment of an indicator, such as is incorporated into the embodiment of the autoinjector explained with reference to FIGS. 1-5. The positions of the transmission part are the same as in the preceding FIGS. 6A-6C, namely, in the stressed, injection-ready state in FIG. 7A, with inserted injection needle in FIG. 7B, and with expelled medication in FIG. 7C. In contrast to the embodiment according to FIGS. 6A-6C, the springs 9 and 11 partially overlap telescopically. This is made possible by the spring sleeve 10, which projects into the spring 11 and receives the spring 9 in its interior. One advantage resulting from this design is the fact that the overall length of the autoinjector can be shorter than in the case of the previously-described configuration of the indicator. Another advantage of this design is that the spring sleeve 10, along with the indicator 12, begins to move only when the injection needle has been inserted and the expelling process begins. This is achieved as follows: As in the case of the previously-described embodiment, here too the springs 9 and 11 are basically connected in series. However, because the elastic force of the spring 9 is limited, since the spring sleeve 10 rests against the catch sleeve 8 on the right, in the initial position according to FIG. 7A the force of spring 11 is greater than the force of spring 9. Starting from this position, the force of spring 11 falls with the traversing of the path 54, but for the time being is still greater than the force of the stressed spring 9. In the position according to FIG. 7B, the force of spring 11 has reached a level that precisely corresponds to the force of the stressed spring 9. Starting from here, during the expelling of the medication, wherein the transmission part 5 moves further to the left by path 55 until it reaches the end position according to FIG. 7C (corresponding to FIGS. 4 and 5), the spring sleeve 10, and with it the indicator 12, moves by the path 56 in proportion to the transmission part 5.

Figures 8, 8A, 8B, 8C:
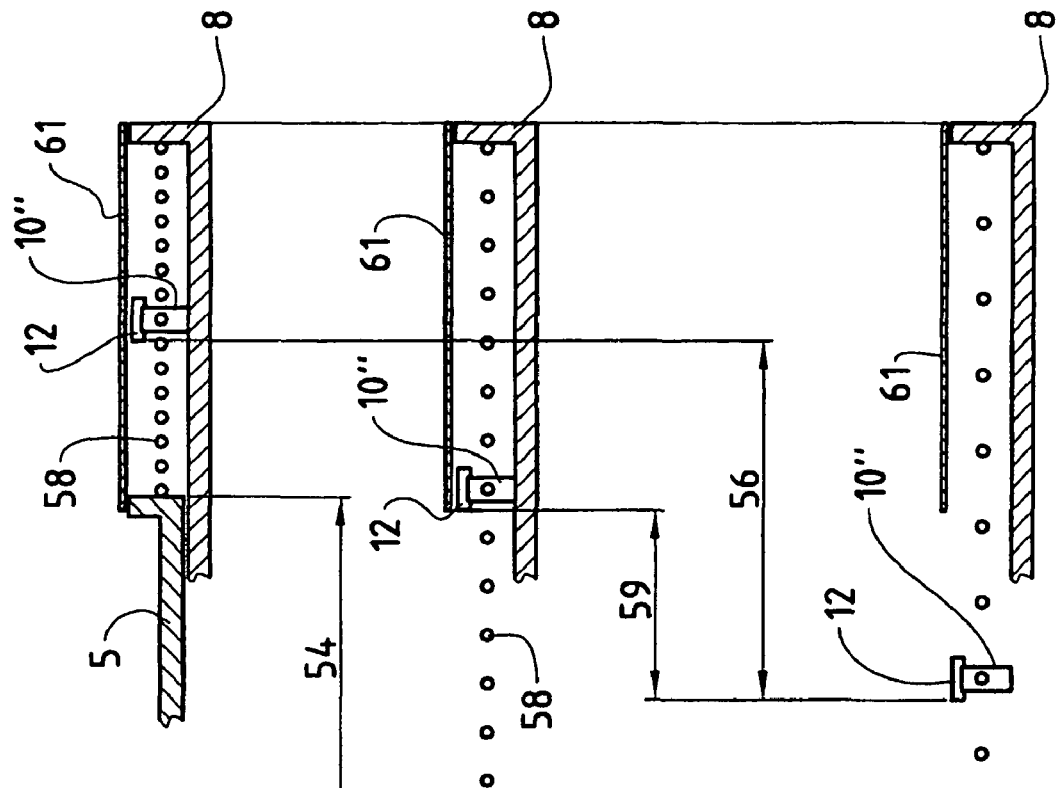
FIG. 8, including
FIGS. 8A-8C, depicts another embodiment of an indicator that operates with spring means.

FIGS. 8A-8C show another embodiment of an indicator. This embodiment is similar to the embodiment depicted in FIGS. 6A-6C. Instead of the springs 9 and 11, here only a single spring 58 is arranged. In the simplest case, the indicator 12 could consist of a marking on the periphery of the spring 58, which marking would be applied, for example, at the longitudinal center of the spring. Preferably, however, in this example the indicator 12 is a ring-shaped part that is connected to the spring 58. Serving to connect the indicator 12 to the spring is an intermediate part, which in this example is labeled 10''. The intermediate part 10'' can be connected to the spring 58 in different ways. For example, the intermediate part 10'' can be ring-shaped, be pushed by the spring 58, and be connected to the latter, for example, through adhesion. Another connection possibility consists in forming the intermediate part in a ring-shaped manner and to dimension its inside diameter such that it is smaller than the outside diameter of the spring 58. In this way, the spring 58 can be screwed into the intermediate part 10''. Finally, the intermediate part 10'' could consist of plastic and be connected to the spring 58 in an injection molding form, whereby a part of the spring 58 is injected around with the plastic material of the intermediate part 10''. The path that the individual parts of the embodiment traverse are the same as in the embodiment according to FIGS. 6A-6C, for which reason the same reference numerals were used for the paths in FIGS. 8A-8C.

FIGS. 9A to 9C show a fourth embodiment of an indicator. In contrast to the embodiments described above, this embodiment is based not on springs, but rather on rolling elements, as will be explained below. The element from which the movement of the indicator is derived is in this example again the piston 5. A part of the latter is shown schematically in the figures and is labeled with 5'. For the sake of simplicity, in FIGS. 9A to 9C no spring is shown. Nevertheless, the movement of the piston 5 for the purpose of inserting the needle and expelling the agent takes place, as in the above-described examples, likewise by means of spring force. Adjacent to this part 5' is another form of the intermediate part, in this example labeled as 10'''. The intermediate part 10''' extends in a longitudinally-displaceable manner between the piston 5' and an extension 1' of the power sleeve 1 or a part fixedly connected to the latter. Also in this example, an indicator 12' is situated on the intermediate part 10''', which indicator can be connected to the intermediate part 10''' as one piece, as shown. The entire path 56 that the intermediate part 10''' can traverse is limited on the left through the resting of the indicator 12' against the power sleeve 1' and on the right through the resting of the indicator 12' against a part 8' connected to the catch sleeve 8. To the last-named part, a cover 61' can be connected as one piece. Incorporated into the intermediate part 10''' are a number of recesses 67, in which rolling element 62 are arranged. When the piston 5' moves toward the left in the drawings during the insertion, the rolling elements 62 roll between the power sleeve 1' and the piston 5', and in the process traverse half of the path that the piston 5 traverses. In this, the rolling elements 62, via the walls of the recesses 67, carry along the intermediate part 10''' and thus, of course, also the indicator 12'. The rolling elements 62 can be formed as balls or as short cylinders. Preferably, three rows of rolling elements 62 are situated so as to distributed at an angular separation of 120° over the circumference of the autoinjector, but any suitable number or arrangement can be used.

FIGS. 10A-10C show another embodiment of an indicator wherein, in the carrying-with of the intermediate part 10''' by the piston 5' an interlocking is ensured, whereby the indicator in this embodiment is not subject to slippage. The interlocking is achieved through at least one toothed wheel 63, which is rotatably supported in a recess 67 of the intermediate part 10''' on an axle 64. The toothed wheel 63 meshes with a toothed region or teeth arranged on the power sleeve 1' and teeth 66 arranged on the piston 5'. During the movement of the piston 5', the toothed wheel 63 is carried along without slippage in a rack-and-pinion-like fashion and, for its part, carries along the intermediate part 10''' via the axle 64. Advantageously, two or three toothed wheels 63 are arranged in a distributed manner over the circumference of the autoinjector. It should be appreciated that any suitable interlocking or engaging structure or surface characteristics may be employed between the wheel(s) and sleeve(s).

While exemplary embodiments, including preferred embodiments, of the present invention have been described herein, it is contemplated that various modifications could be made without deviating from the spirit of the present invention. Accordingly, it is intended that the scope of the present invention be dictated by the appended claims.

The invention claimed is:

1. A device for automatically injecting an agent, said device comprising a receptacle for the agent, which receptacle is displaceable, together with an injection needle connected thereto, inside a housing for the purpose of inserting the injection needle into a patient, a syringe piston that is displaceable inside the receptacle for the purpose of expelling the agent, an indicator, wherein an axial displacement path of the indicator visible from the outside shows progress of expelling the agent from a beginning of the expelling to an end of the expelling, said visible axial displacement path being shorter than a total distance of displacement of the syringe piston relative to the housing, and a transmission part movable along a first partial path for inserting the injection needle and a second partial path for expelling the agent and operably connected to the indicator by at least one spring element such that said indicator moves along the visible indicator displacement path in response to the transmission part expelling the agent.

2. The device according to claim 1, wherein the at least one spring element is operably effective on the transmission part and a support part fixedly connected to the housing.

3. The device according to claim 2, wherein the at least one spring element has two ends and the indicator is operably connected to the at least one spring element at a location between the two ends.

4. The device according to claim 1, further comprising at least one additional spring element, the transmission part displaceable by the at least one spring element such that the at least one spring element is operably effective on the transmission part and an intermediate part, and the at least one additional spring element operably effective on the intermediate part and a support part fixedly connected to the housing, wherein the indicator is connected to the intermediate part.

5. The device according to claim 1, wherein the indicator is ring-shaped.

6. The device according to claim 1, further comprising at least one additional spring element, wherein said indicator is additionally effectively acted upon by the at least one additional spring element moving the indicator along the visible indicator displacement path in response to expelling the agent.

7. The device according to claim 1, further comprising a intermediate part operably coupled with the indicator, wherein said indicator is effectively acted upon by the intermediate part moving the indicator along the visible indicator displacement path in response to expelling the agent.

8. The device according to claim 7, wherein the intermediate part comprises a spring sleeve.

9. The device according to claim 7, wherein the intermediate part comprises at least one rolling element.

10. The device according to claim 7, wherein the intermediate part comprises a toothed wheel.

11. The device according to claim 7, wherein the intermediate part comprises a ring-shaped element physically connected to the at least one spring element.

* * * * *